(12) United States Patent
Honegger

(10) Patent No.: US 12,303,715 B2
(45) Date of Patent: May 20, 2025

(54) METHODS AND APPARATUS FOR AUTOMATICALLY DETERMINING RADIOABLATION TREATMENT RISK

(71) Applicant: Varian Medical Systems, Inc., Palo Alto, CA (US)

(72) Inventor: Jonas Honegger, Zurich (CH)

(73) Assignee: Varian Medical Systems, Inc., Palo Alto, CA (US)

( * ) Notice: Subject to any disclaimer, the term of this patent is extended or adjusted under 35 U.S.C. 154(b) by 368 days.

(21) Appl. No.: 17/810,159

(22) Filed: Jun. 30, 2022

(65) Prior Publication Data

US 2024/0001150 A1    Jan. 4, 2024

(51) Int. Cl.
| | | |
|---|---|---|
| *G16H 50/20* | (2018.01) | |
| *A61N 5/10* | (2006.01) | |
| *G16H 20/40* | (2018.01) | |

(52) U.S. Cl.
CPC ......... *A61N 5/1039* (2013.01); *A61N 5/1031* (2013.01); *G16H 20/40* (2018.01)

(58) Field of Classification Search
None
See application file for complete search history.

(56) References Cited

U.S. PATENT DOCUMENTS

| | | | |
|---|---|---|---|
| 10,799,716 B2 | 10/2020 | Morgas et al. | |
| 11,826,560 B2 * | 11/2023 | Zhang | G16H 20/40 |
| 2020/0104695 A1 | 4/2020 | Laaksonen et al. | |
| 2021/0236854 A1 * | 8/2021 | Voronenko | A61N 5/1039 |
| 2022/0126117 A1 | 4/2022 | Voronenko et al. | |
| 2023/0293907 A1 * | 9/2023 | Shade | A61N 5/1031 600/1 |
| 2023/0302297 A1 * | 9/2023 | Lachaine | A61N 5/1039 |

FOREIGN PATENT DOCUMENTS

| | | | | |
|---|---|---|---|---|
| CN | 116171184 A | * | 5/2023 | ............ A61N 5/103 |
| CN | 117178291 A | * | 12/2023 | ............ G06N 20/00 |
| WO | 2018222751 A1 | | 12/2018 | |
| WO | 2022051068 A1 | | 3/2022 | |
| WO | WO-2022256782 A1 | * | 12/2022 | ............ A61N 5/103 |

OTHER PUBLICATIONS

Oh, et al., "Deformable image registration in radiation therapy", Radiation Oncology Journal, vol. 35, No. 2, Jun. 30, 2017 (Jun. 30, 2017), pp. 101-111.
PCT International Search Report and Written Opinion of PCT/US2023/024774 issued Sep. 18, 2023.

* cited by examiner

*Primary Examiner* — Mohammed Rachedine
(74) *Attorney, Agent, or Firm* — Duane Morris LLP

(57) ABSTRACT

Systems and methods for cardiac radioablation treatment and planning are disclosed. In some examples, a computing device receives a first image of a patient that was captured for treatment planning. The computing device also receives target definition data characterizing a target area of the patient for treatment. Further, the computing device receives a second image of the patient captured on the day of, and prior to, treatment. The computing device determines whether there is a risk to an organ of the patient based on the first image, the target definition data, and the second image. The computing device also provides for display an indication of risk to the patient based on the determination. For example, the indication of risk can include a treatment target region and an organ at risk region superimposed over the second image. In some examples, the indication of risk includes expected dosage levels.

20 Claims, 10 Drawing Sheets

METHODS AND APPARATUS FOR AUTOMATICALLY DETERMINING RADIOABLATION TREATMENT RISK

FIELD

Aspects of the present disclosure relate in general to medical diagnostic and treatment systems and, more particularly, to providing radioablation diagnostic, treatment planning, and delivery systems for treatment of conditions, such as cardiac arrhythmias.

BACKGROUND

Various technologies can be employed to capture or image a patient's metabolic, electrical, and anatomical information. For example, positron emission tomography (PET) is a metabolic imaging technology that produces tomographic images representing the distribution of positron emitting isotopes within a body. Computed Tomography (CT) and Magnetic Resonance Imaging (MRI) are anatomical imaging technologies that create images using x-rays and magnetic fields respectively. Images from these exemplary technologies can be combined with one another to generate composite anatomical and functional images, such as PET/CT or PET/MRI. For example, software systems, such as Velocity™ software from Varian Medical Systems, Inc., can combine different types of images using an image fusion process to deform and/or register images to produce a combined image.

Medical professionals, such as electrophysiologists and radiation oncologists, rely on these images to identify target areas for treatment. For example, in cardiac radioablation, medical professionals work together to diagnose cardiac arrhythmias, identify regions for ablation, prescribe radiation treatment, and create radioablation treatment plans. Prior to treating a patient, the patient may be scanned using one or more of the anatomical imaging technologies to obtain images of the patient. An electrophysiologist may identify one or more regions (e.g., targets) of an organ of the patient for treatment, such as the patient's heart for treatment of cardiac arrhythmias, based on the images. Once a target region is defined by the electrophysiologist, a radiation oncologist may prescribe radiation treatment including, for example, a number of fractions of radiation to be delivered, a radiation dose to be delivered to a target region (e.g., within the regions identified by the electrophysiologist), and a maximum dose that can be delivered to adjacent organs at risk. Further, a dosimetrist may create a radioablation treatment plan based on the prescribed radiation treatment. In some examples, the radiation oncologist may review and approve the treatment plan. In addition, the electrophysiologist may review the location, size, and shape of the defined target region to confirm the target location as defined by the radioablation treatment plan is appropriate.

SUMMARY

Systems and methods for cardiac radioablation treatment and planning are disclosed. In some examples, prior to a time of treatment, an imaging device scans a patient using one or more of any suitable anatomical imaging technology, such as CT, MM, or PET, to obtain one or more images of the patient. The images may identify an organ to be treated, as well as healthy organs that do not require treatment but nevertheless may be close to the organ, or a portion of the organ, to be treated (e.g., OARs). A treatment plan is then developed based on the obtained images. For example, a medical professional may identify one or more regions of the organ for treatment based on the images. Further, a radiation oncologist may determine a radiation dose to be delivered to a target region based on the regions identified by the medical professional and the images. Further, the treatment planning system may store the treatment planning (TP) images and the target definition data characterizing the target region and the radiation dose to be delivered in a data repository. The patient may then be scheduled for treatment based on the treatment plan, typically days or weeks after the TP images were obtained.

On the day of treatment, an imaging device, such as one located on or near a treatment device, scans the patient to obtain one or more additional images of the patient (i.e., treatment delivery (TD) images). Further, the treatment application device obtains the target definition data characterizing the target region and the radiation dose from the data repository, and displays the target region over one of the TD images. For instance, the treatment application device may determine a location of the target region within the one or more TD images, and may provide for display an overlay of the target region at the determined location over one of the TD images. Before treatment, a medical professional, such as the medical professional that will be controlling the treatment device to provide the dosage to the patient, may determine whether it is still acceptable to provide the dosage to the target region based on positioning of organs, such as OARs, as illustrated by the displayed overlay of the target region at the determined location over the TD images.

In some examples, the treatment application system obtains the TP images and the target definition data from the data repository and automatically determines whether there is a risk to an organ (e.g., any OAR) of the patient based on the TP images, the target definition data, and the one or more TD images. For instance, the treatment application system may compute one or more dose-volume histograms (DVHs) based on a relative positioning of the target region to one or more OARs within the additional image, and may determine whether one or more DVH dose constraints are violated based on the computed DVHs. For example, the treatment application system may determine that a DVH dose constraint is violated if a portion of an OAR is at risk to receive a dosage above a predetermined threshold if the radiation dose is applied to the target region. In other examples, the treatment application system may determine a relative positioning between an organ, such as an OAR, in an TP image (e.g., one obtained prior to treatment planning) and a TD image (e.g., one obtained for treatment delivery), and may determine that an OAR dose constraint is violated if the organ has moved more than a predetermined distance. Yet in other examples, the treatment application system may determine a positioning (e.g., distance) between the target region and an organ, such as an OAR, in the TP image, and another relative positioning between the target region in a TD image and the same organ. The treatment application system may determine that an OAR dose constraint is violated based on the relative positioning determined for each of the TP and TD images. For instance, the treatment planning system may compare (e.g., subtract) the determined relative positioning, and may determine an OAR dose constraint is violated based on the comparison (e.g., the difference is at or beyond a predetermined threshold).

The treatment application system may generate an alert if any risks are determined. For instance, the treatment application system may provide one or more of a visual or auditory alert notifying the medical professional of the determined risk. In some examples, the medical professional may provide input to the treatment planning system to alter the target region based on the alerts. In some examples, the treatment application system may prevent any dosage from being supplied to the patient until the alert is "cleared" by the medical professional. In some examples, a clearance from at least a minimum number of medical professionals (e.g., two) is required before the treatment application system allows dosage to be provided to the patient. For instance, the treatment application system may require at least two medical professionals to input their credentials (e.g., log in) and clear the alert before allowing any dosage to be provided to the patient.

In some embodiments, a system includes a database, and a computing device communicatively coupled to the database. The computing device is configured to receive a first image of a patient (e.g., a TP image). For example, the computing device may receive magnetic resonance (MR) image data, computed tomography (CT) image data, or positron emission tomography (PET) image data from an image scanning system. The first image may have been captured during treatment planning (e.g., before the day of treatment). The computing device is also configured to receive target definition data characterizing a target area of the patient for treatment. The target definition data may include, for example, DVH data characterizing expected dosage levels to various portions of the target area. Further, the computing device is configured to receive a second image of the patient (e.g., a TD image). The second image may be captured on the day of treatment (e.g., while the patient is on the treatment table prior to receiving the prescribed treatment). The computing device is configured to determine whether there is a risk to an organ (e.g., an OAR) of the patient based on the first image, the target definition data, and the second image. The computing device is further configured to provide for display an indication of risk based on the determination.

In some embodiments, a computer-implemented method includes receiving a first image of a patient (e.g., a TP image). The first image may have been captured during treatment planning (e.g., before the day of treatment). The computer-implemented method also includes receiving target definition data characterizing a target area of the patient for treatment. The target definition data may include, for example, DVH data characterizing expected dosage levels to various portions of the target area. Further, the computer-implemented method includes receiving a second image of the patient (e.g., a TD image). The second image may be captured on the day of treatment (e.g., while the patient is on the treatment table prior to receiving the prescribed treatment). The computer-implemented method also includes determining whether there is a risk to an organ (e.g., an OAR) of the patient based on the first image, the target definition data, and the second image. The computer-implemented method further includes providing for display an indication of risk based on the determination.

In some examples, a non-transitory computer readable medium storing instructions that, when executed by at least one processor, cause the at least one processor to perform operations including receiving a first image of a patient (e.g., a TP image). The first image may have been captured during treatment planning (e.g., before the day of treatment). The operations also include receiving target definition data characterizing a target area of the patient for treatment. The target definition data may include, for example, DVH data characterizing expected dosage levels to various portions of the target area. Further, the operations include receiving a second image of the patient (e.g., a TD image). The second image may be captured on the day of treatment (e.g., while the patient is on the treatment table prior to receiving the prescribed treatment). The operations also include determining whether there is a risk to an organ (e.g., an OAR) of the patient based on the first image, the target definition data, and the second image. The operations further include providing for display an indication of risk based on the determination.

In some examples, a system comprising at least one computing device includes a means for receiving a first image of a patient (e.g., a TP image). The first image may have been captured during treatment planning (e.g., before the day of treatment). The system also includes a means for receiving target definition data characterizing a target area of the patient for treatment. The target definition data may include, for example, DVH data characterizing expected dosage levels to various portions of the target area. Further, the system includes a means for receiving a second image of the patient (e.g., a TD image). The second image may be captured on the day of treatment (e.g., while the patient is on the treatment table prior to receiving the prescribed treatment). The system also includes a means for determining whether there is a risk to an organ (e.g., an OAR) of the patient based on the first image, the target definition data, and the second image. The system further includes a means for providing for display an indication of risk based on the determination.

In some embodiments, a system includes a database, and a computing device communicatively coupled to the database. The computing device is configured to receive a first image of a patient. For example, the computing device may receive magnetic resonance (MR) image data, computed tomography (CT) image data, or positron emission tomography (PET) image data from an image scanning system. The first image may have been captured during treatment planning (e.g., before the day of treatment). The computing device is also configured to display an indication of a first organ at risk area and a first target area superimposed over the first image. Further, the computing device is configured to receive a second image of the patient. The second image may be captured on the day of treatment (e.g., while the patient is on the treatment table prior to receiving the prescribed treatment). The computing device is also configured to determine a second organ at risk area within the second image. The second organ at risk area of the second image may include a same organ as an organ within the first organ at risk area of the first image. For instance, the second organ at risk area of the second image may overlap at least partially with the first organ at risk area of the first image. The computing device is further configured to determine a second target area within the second image based on the first target area, the first organ at risk area, and the second organ at risk area. The computing device is also configured to provide for display an indication of the second organ at risk area and the second target area superimposed over the second image.

In some embodiments, a computer-implemented method includes receiving a first image of a patient. The first image may have been captured during treatment planning (e.g., before the day of treatment). The computer-implemented method also includes displaying an indication of a first organ at risk area and a first target area superimposed over the first image. Further, the computer-implemented method includes receiving a second image of the patient. The second image may be captured on the day of treatment (e.g., while the patient is on the treatment table prior to receiving the prescribed treatment). The computer-implemented method further includes determining a second organ at risk area within the second image. The computer-implemented method also includes determining a second target area within the second image based on the first target area, the first organ at risk area, and the second organ at risk area. The computer-implemented method further includes providing for display an indication of the second organ at risk area and the second target area superimposed over the second image.

In some examples, a non-transitory computer readable medium storing instructions that, when executed by at least one processor, cause the at least one processor to perform operations including receiving a first image of a patient. The first image may have been captured during treatment planning (e.g., before the day of treatment). The operations also include displaying an indication of a first organ at risk area and a first target area superimposed over the first image. Further, the operations include receiving a second image of the patient. The second image may be captured on the day of treatment (e.g., while the patient is on the treatment table prior to receiving the prescribed treatment). The operations further include determining a second organ at risk area within the second image. The operations also include determining a second target area within the second image based on the first target area, the first organ at risk area, and the second organ at risk area. The operations further include providing for display an indication of the second organ at risk area and the second target area superimposed over the second image.

In some examples, a system comprising at least one computing device includes a means for receiving a first image of a patient. The first image may have been captured during treatment planning (e.g., before the day of treatment). The system also includes a means for displaying an indication of a first organ at risk area and a first target area superimposed over the first image. Further, the system includes a means for receiving a second image of the patient. The second image may be captured on the day of treatment (e.g., while the patient is on the treatment table prior to receiving the prescribed treatment). The system further includes a means for determining a second organ at risk area within the second image. The system also includes a means for determining a second target area within the second image based on the first target area, the first organ at risk area, and the second organ at risk area. The system further includes a means for providing for display an indication of the second organ at risk area and the second target area superimposed over the second image.

BRIEF DESCRIPTION OF THE DRAWINGS

The features and advantages of the present disclosures will be more fully disclosed in, or rendered obvious by the following detailed descriptions of example embodiments. The detailed descriptions of the example embodiments are to be considered together with the accompanying drawings wherein like numbers refer to like parts and further wherein.

DETAILED DESCRIPTION

Figure 1:
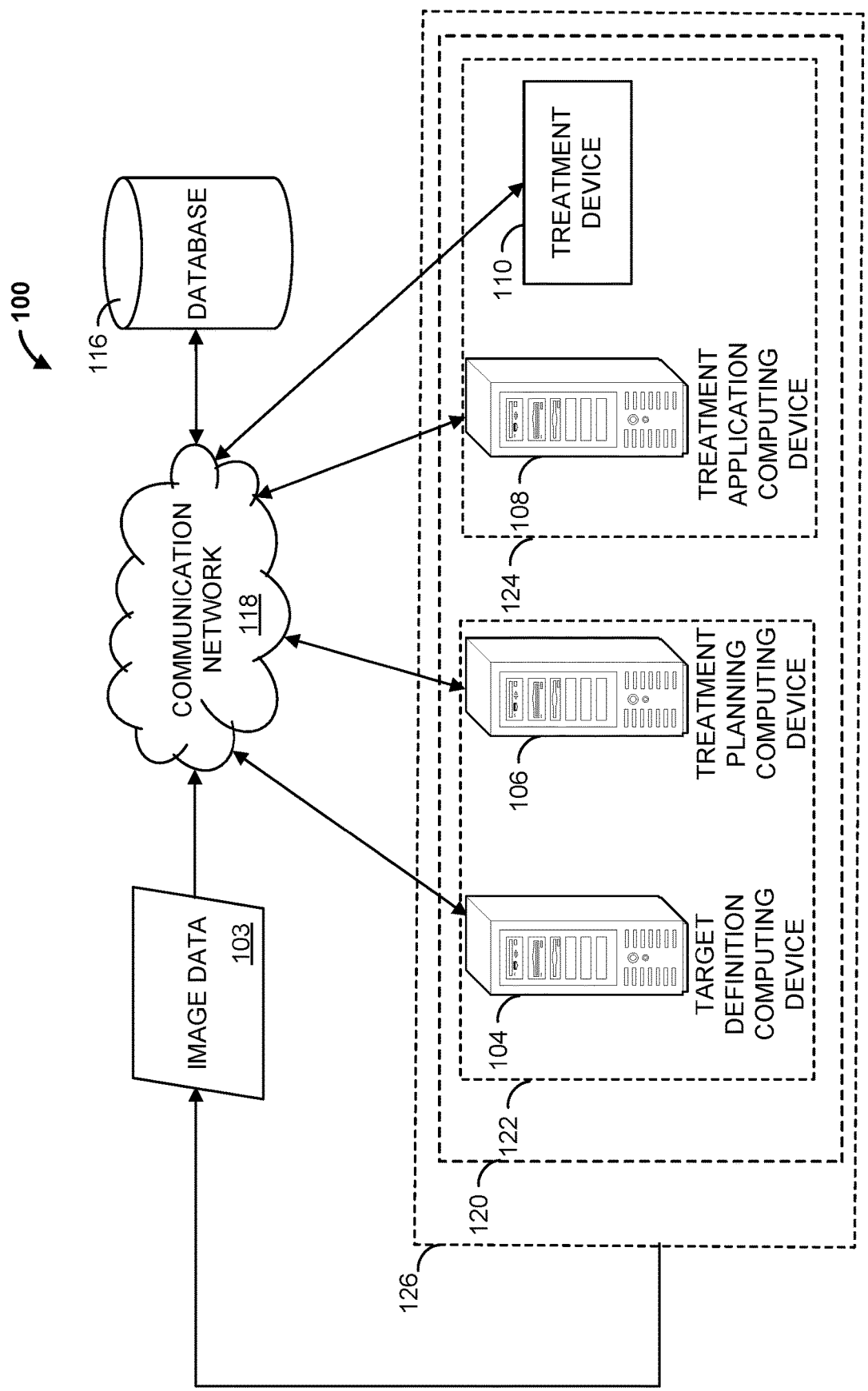
FIG. 1 illustrates a treatment planning and application system, in accordance with some embodiments.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, electrically, wired, wirelessly, or otherwise, such that the connection allows the pertinent devices or components to operate (e.g., communicate) with each other as intended by virtue of that relationship.

Properly identifying and defining the target region of a patient's organ for treatment is essential for developing and optimizing the treatment plan. For example, delivering dosages to areas not intended may cause harm to the patient, such as when the prescribed dosage is applied to portions of any organ at risk (OAR) not intended to receive treatment. For instance, CRA treatments are typically planned with a high single fraction radiation dose to a portion of the cardiac anatomy. Some organs and structures in the vicinity of the treatment area are highly sensitive to external beam radiation such as the stomach and the esophagus. Protecting these structures from high dose of radiation is a major objective when planning CRA treatments as the effects of exceeding dose limits for these organs can be severe.

In at least some instances, the anatomical arrangement of a patient's organ may present differently on the day of treatment compared to when the patient was originally scanned to determine the patient's treatment plan. When this happens, there is no guarantee that any dosage to any OARs determined in the intimal treatment plan still holds true. Indeed, depending on any changes to the patient's anatomical arrangement, OARs may now be subject to higher amounts of dosage than was originally determined in the initial treatment plan. Among other advantages, the embodiments described herein may improve radioablation treatment planning systems used by medical professionals, such as cardiac radioablation treatment systems used for cardiac radioablation treatment planning, by automatically determining whether OARs of a patient are at unacceptable higher levels of risk on treatment day.

Turning to the drawings, FIG. 1 illustrates a block diagram of a treatment planning and application system 100 that includes an imaging device 102, a treatment planning computing device 106, a treatment application computing device 108, one or more target definition computing devices 104, a treatment device 110, and a database 116 communicatively coupled over communication network 118. Imaging device 102 may be, for example, a CT scanner, an MR scanner, a PET scanner, an electrophysiologic imaging device, or an electrocardiographic (ECG) imager. In some examples, imaging device 102 may be PET/CT scanner or a PET/MR scanner. Treatment device 110 may be a photon (such as a Varian™ TrueBeam radiotherapy system) or proton radiotherapy device. In some examples, target definition computing device 104, treatment planning computing device 106, treatment application computing device 108, and treatment device 100 may be part of a cardiac radioablation treatment system 126 that allows for radioablation treatment to a patient. For example, radioablation treatment system 126 may allow for the delivery of defined doses to one or more treatment areas of the patient.

Each target definition computing device 104, treatment planning computing device 106, and treatment application computing device 108 can be any suitable computing device that includes any suitable hardware or hardware and software combination for processing data. For example, each can include one or more processors, one or more field-programmable gate arrays (FPGAs), one or more application-specific integrated circuits (ASICs), one or more state machines, digital circuitry, or any other suitable circuitry. In addition, each can transmit data to, and receive data from, communication network 118. For example, each target definition computing device 104, treatment planning computing device 106, and treatment application computing device 108 can be a server such as a cloud-based server, a computer, a laptop, a mobile device, a workstation, or any other suitable computing device.

Figure 2:
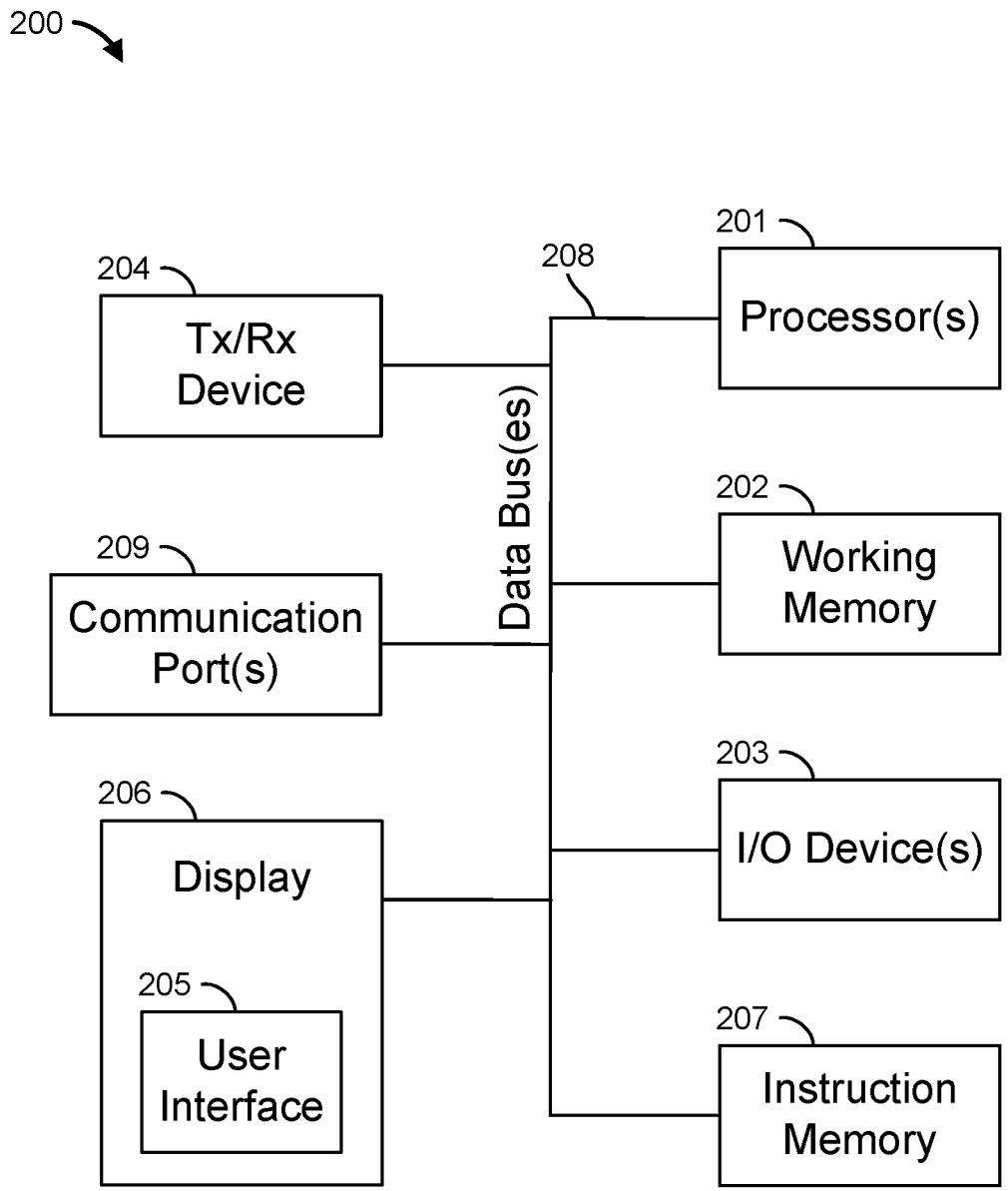
FIG. 2 illustrates a block diagram of an exemplary computing device, in accordance with some embodiments.

For example, FIG. 2 illustrates an exemplary computing device 200, which may be an example of any of target definition computing device 104, treatment planning computing device 106, and treatment application computing device 108. Exemplary computing device 200 includes one or more processors 201, working memory 202, one or more input-output (I/O) devices 203, instruction memory 207, a transceiver 204, one or more communication ports 207, and a display 206, all operatively coupled to one or more data buses 208. Data buses 208 allow for communication among the various devices. Data buses 208 can include wired, or wireless, communication channels.

Processors 201 can include one or more distinct processors, each having one or more cores. Each of the distinct processors can have the same or different structure. Processors 201 can include one or more central processing units (CPUs), one or more graphics processing units (GPUs), application specific integrated circuits (ASICs), digital signal processors (DSPs), and the like.

Instruction memory 207 can store instructions that can be accessed (e.g., read) and executed by processors 201. For example, instruction memory 207 can be a non-transitory, computer-readable storage medium such as a read-only memory (ROM), an electrically erasable programmable read-only memory (EEPROM), flash memory, a removable disk, CD-ROM, any non-volatile memory, or any other suitable memory. Processors 201 can be configured to perform a certain function or operation by executing code, stored on instruction memory 207, embodying the function or operation. For example, processors 201 can be configured to execute code stored in instruction memory 207 to perform one or more of any function, method, or operation disclosed herein.

Additionally processors 201 can store data to, and read data from, working memory 202. For example, processors 201 can store a working set of instructions to working memory 202, such as instructions loaded from instruction memory 207. Processors 201 can also use working memory 202 to store dynamic data created during the operation of computing device 200. Working memory 202 can be a random access memory (RAM) such as a static random access memory (SRAM) or dynamic random access memory (DRAM), or any other suitable memory.

Input-output devices 203 can include any suitable device that allows for data input or output. For example, input-output devices 203 can include one or more of a keyboard, a touchpad, a mouse, a stylus, a touchscreen, a physical button, a speaker, a microphone, or any other suitable input or output device.

Communication port(s) 209 can include, for example, a serial port such as a universal asynchronous receiver/transmitter (UART) connection, a Universal Serial Bus (USB) connection, or any other suitable communication port or connection. In some examples, communication port(s) 209 allows for the programming of executable instructions in instruction memory 207. In some examples, communication port(s) 209 allow for the transfer (e.g., uploading or downloading) of data, such as image data.

Display 206 can be any suitable display, such as a 3D viewer or a monitor. Display 206 can display user interface 205. User interfaces 205 can enable user interaction with computing device 200. For example, user interface 205 can be a user interface for an application that allows a user (e.g., a medical professional) to view or manipulate models to define a target region of treatment for a patient as described herein. In some examples, the user can interact with user interface 205 by engaging input-output devices 203, such as a mouse. In some examples, display 206 can be a touchscreen, where user interface 205 is displayed on the touchscreen. In some examples, display 206 displays images of scanned image data (e.g., image slices).

Transceiver 204 allows for communication with a network, such as the communication network 118 of FIG. 1. For example, if communication network 118 of FIG. 1 is a cellular network, transceiver 204 is configured to allow communications with the cellular network. In some examples, transceiver 204 is selected based on the type of communication network 118 exemplary computing device 200 will be operating in. Processor(s) 201 is operable to receive data from, or send data to, a network, such as communication network 118 of FIG. 1, via transceiver 204.

Referring back to FIG. 1, database 116 can be a remote storage device (e.g., including non-volatile memory), such as a cloud-based server, a disk (e.g., a hard disk), a memory device on another application server, a networked computer, or any other suitable remote storage. In some examples, database 116 can be a local storage device, such as a hard drive, a non-volatile memory, or a USB stick, to one or more of target definition computing device 104, treatment planning computing device 106, and treatment application computing device 108.

Communication network 118 can be a WiFi network, a cellular network such as a 3GPP® network, a Bluetooth® network, a satellite network, a wireless local area network (LAN), a network utilizing radio-frequency (RF) communication protocols, a Near Field Communication (NFC) network, a wireless Metropolitan Area Network (MAN)

connecting multiple wireless LANs, a wide area network (WAN), or any other suitable network. Communication network 118 can provide access to, for example, the Internet.

Imaging device 102 is operable to scan images, such as images of a patient's organs, and provide image data 103 (e.g., measurement data) identifying and characterizing the scanned images to communication network 118. Alternatively, imaging device 102 is operable to acquire electrical imaging such as cardiac ECG images. For example, imaging device 102 may scan a patient's structure (e.g., organ), and may transmit image data 103 identifying one or more slices of a 3D volume of the scanned structure over communication network 118 to one or more of treatment planning computing device 106 and treatment application computing device 108. In some examples, imaging device 102 stores image data 103 in database 116, and one or more of treatment planning computing device 106 and treatment application computing device 108 may retrieve the image data 103 from database 116.

In some examples, treatment planning computing device 106 is operable to communicate with treatment application computing device 108 and target definition computing device 104 over communication network 118. In some examples, one or more of treatment planning computing device 106, treatment application computing device 108, and target definition computing device 104 communicate with each other via database 116 (e.g., by storing and retrieving data from database 116). In some examples, one or more of treatment planning computing devices 106 and one or more treatment application computing devices 108 are part of a cloud-based network that allows for the sharing of resources and communication with each device.

In some examples, one or more exemplary computing devices 104 and 106 are located in a first area 122 of a medical facility 120, while computing device 108 and treatment device 100 are located in a second area 124 of the medical facility 120. As such, treatment planning and application system 100 allows multiple EPs to collaborate to finalize a target area.

Generating Images Prior to Treatment Application

As described herein, prior to treatment planning (e.g., before the time of treatment), image scanning device 102 may scan a patient to obtain one or more treatment planning (TP) images. The images may identify the patient's anatomical arrangement by illustrating various organs of the patient. Further, image scanning device 102 may store image data 103 characterizing the images in database 116. Based on the images, one or more medical professionals operating one or more treatment planning computing devices 106 may determine a treatment plan for the patient. The treatment plan may identify a treatment target region of the patient, as well as a radiation dose to be delivered to the target region.

For instance, treatment planning computing device 106 may execute an application that causes the generation of a user interface (e.g., user interface 205) which may be displayed to a medical professional, such as a dosimetrist. The executed application may assist the medical professional in defining a target area of a patient for treatment. For example, a dosimetrist may operate treatment planning computing device 106 to define a target region of treatment for a patient. In some examples, the treatment plan may also identify one or more OAR regions within the TP images. Treatment planning computing devices 106 may store target definition data characterizing the treatment plan within database 116.

On the day of (e.g., just before) treatment, the patient is scanned, for example using a linear accelerator integrated kV-conebeam CT, to obtain one or more treatment delivery (TD) images. Treatment application computing device 108 may also obtain one or more of the TP images, as well as the target definition data, from database 116. While the TP images may identify an original anatomical arrangement of the patient at the time the TP images were captured, the TD images may identify a current anatomical arrangement of the patient. In at least some instances, the current anatomical arrangement of the patient may not be the same as the original anatomical arrangement of the patient. As such, the treatment plan originally prescribed for the patient may not be appropriate, as the dosage may be applied to the patient at areas and dosage levels not previously accounted for.

Figure 4A:
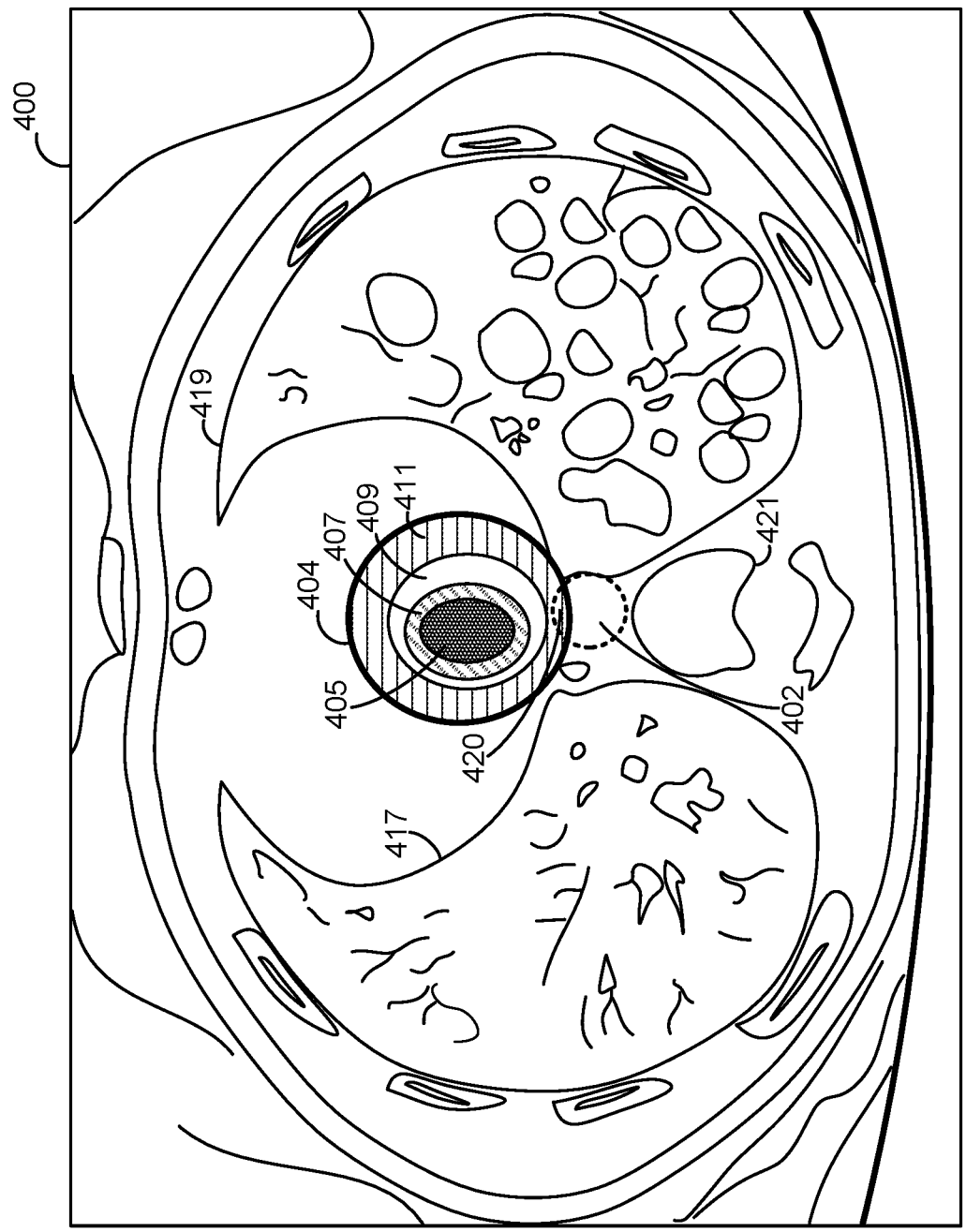
FIGS. 4A and 4B illustrates images identifying a target region and an organ at risk (OAR) region, in accordance with some embodiments.

For instance, on the day of treatment, treatment application computing device 108 may display a TP image obtained from image scanning device 102 for treatment planning, along with an overlay of indications of the treatment target region and one or more OAR regions as defined by the target definition data. FIG. 4A illustrates a TP image 400 that identifies various structures, such as structures 417, 419, and 421, and further includes a TP OAR region 402 defined by a circle in dashed lines, as well as an TP treatment target area 404. As illustrated, TP treatment target area 404 identifies various portions distinguished by hashing technique, where each portion corresponds to a differing level (e.g., DVH level) of expected dosage. For example, first portion 405 may identify an area of TP treatment target area 404 expected to receive a highest dosage. Further, second portion 407 may identify an area of TP treatment target area 404 expected to receive a next highest dosage (e.g., less than first portion 405), and third portion 409 may identify an area of TP treatment target area 404 expected to receive a next highest dosage (i.e., less than second portion 407). Fourth portion 411 may identify an area of TP treatment target area 404 expected to receive the least dosage levels (i.e., dosage less than that of the third portion 409 but greater than a minimum amount of dosage, such as no dosage at all). In this example, TP OAR region 402 overlaps at overlap region 420 with fourth region 411, but not with any of first region 405, second region 407, and third region 409.

Referring back to FIG. 1, treatment application computing device 108 may also display, on the day of treatment, a TP image along with an overlay of indications of the treatment target region as defined by the target definition data and one or more OAR regions corresponding to the TP image. The OARs may be delineated manually or automatically using various available algorithms. For instance, treatment application computing device 108 may display the TP image, and may receive input from a medical professional, such as an dosimetrist, that characterizes one or more corresponding OAR regions. If done manually, the dosimetrist may, for example, "draw" the corresponding OAR region onto the display with user interface tools provided by the treatment planning software. Treatment application computing device 108 may generate OAR data characterizing the OAR region based on the input, and may store the OAR data in database 116.

Figure 4B:
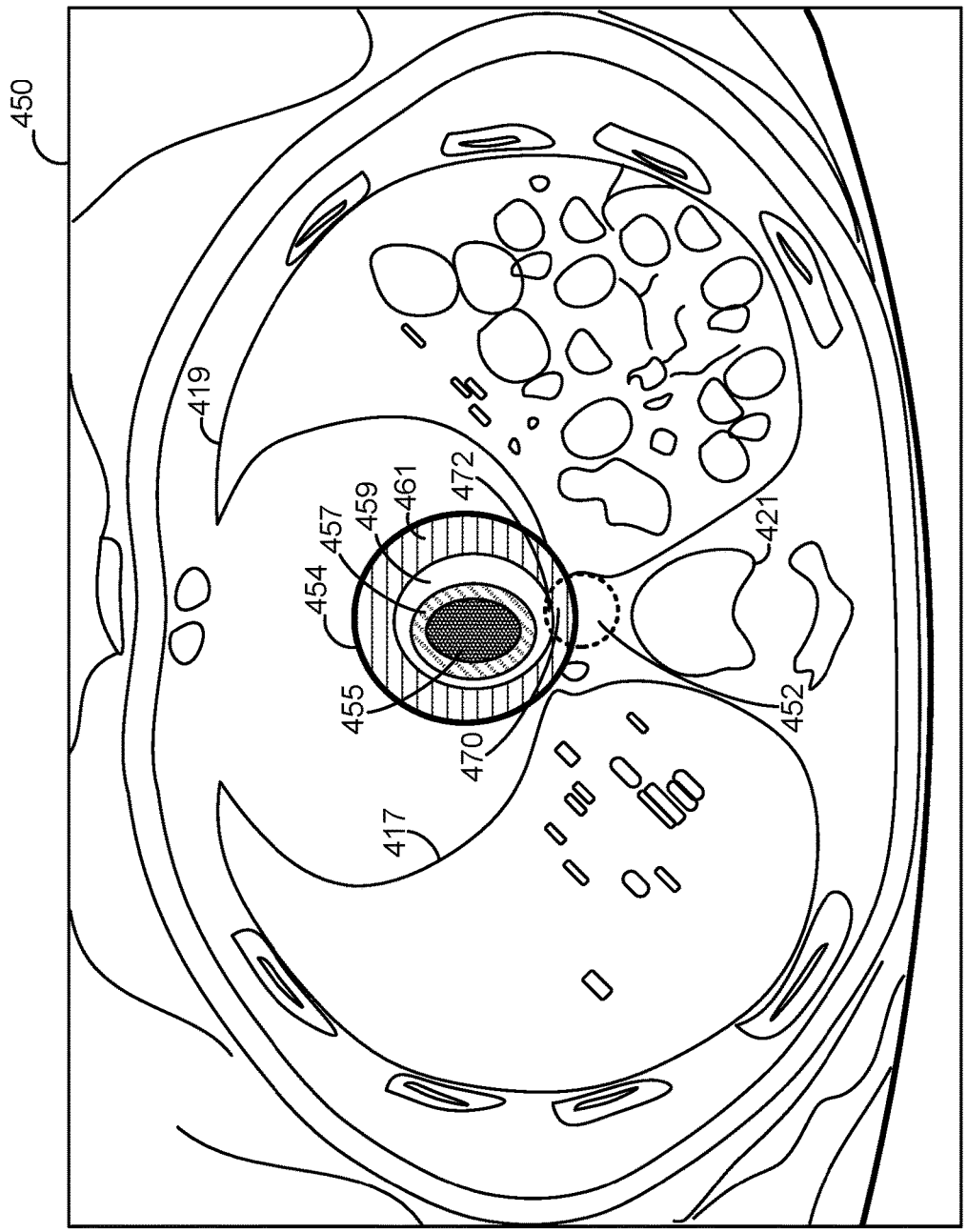

Treatment application computing device 108 may display the TP image along with an overlay of an indication of the treatment target region as defined by the target definition data, as well as any determined OAR regions (e.g., as defined by the OAR data). For instance, FIG. 4B illustrates a TD image 450 that includes a TD OAR region 452 as well as TD treatment target area 454. TD OAR region 452 may correspond to the TP OAR region determined by the medical professional (e.g., based on TD image 450). Further, and similar to TP treatment target area 404, TD treatment target area 454 identifies various portions distinguished, in this example, by differing hashing, where each portion corresponds to a differing level (e.g., DVH level) of expected dosage. For example, first portion 455 may identify an area of TD treatment target area 454 expected to receive a highest dosage. Further, second portion 457 may identify an area of TD treatment target area 454 expected to receive a next highest dosage (e.g., less than first portion 405), and third portion 459 may identify an area of TD treatment target area 454 expected to receive a next highest dosage (i.e., less than second portion 457). Fourth portion 461 may identify an area of TD treatment target area 454 expected to receive the least dosage levels (i.e., dosage less than that of the third portion 459 but greater than a minimum amount of dosage, such as no dosage at all).

In some examples, treatment application computing device 108 determines TD treatment target area 454 based on applying one or more transformation models (e.g., algorithms) to one or more of the TP treatment target area 404, the TP OAR region 402, and the TD OAR region 452. For instance, treatment application computing device 108 may identify corresponding structures, such as structures 417, 419, and 421, between TP image 400 and TD image 450. In some examples, treatment application computing device 108 identifies the corresponding structures based on inputting the TP image 400 and the TD image 450 to a trained machine learning model, and receiving, as output, elements of output data characterizing similar structures between the input images. In some examples, a medical professional provides input to treatment application computing device 108 to identify similar structures between the TP image 400 and the TD image 450.

Further, and based on the determined corresponding structures, treatment application computing device 108 applies a transformation model to determine a mapping between TP image 400 and TD image 450. For instance, treatment application computing device 108 may determine a location of the structures in each of the TP image 400 and the TD image 450. The locations may be each defined by a bounding box, which includes a range in each of two dimensions (e.g., an X range and a Y range). In some examples, the locations identify a range of pixels of the corresponding image in each of a number of dimensions, such as two or three dimensions. In some examples, the locations identify a single point (e.g., pixel) of the image based on a two-dimensional coordinate (e.g., X, Y location). The single point may be a center of each structure, for example. Treatment application computing device 108 may apply the transformation model to the determined locations to determine the mapping (e.g., a two dimensional mapping from TP image 400 to TD image 454). The transformational model may be, for instance, a Deformable Image Registration (DIR) algorithm. The DIR algorithm may be executed to map spatial correspondence across two images. For example, the output generated by the executed DIR algorithm may include a vector that defines the mapping between the two images.

Further, and based on TP treatment target area 404 and the determined mapping, treatment application computing device 108 generates image data characterizing TD treatment target area 454. In this example, TD treatment target area 454 overlaps with fourth portion 461 at overlap region 470, and also overlaps with third portion 459 at overlap region 472. For example, the area of overlap region 420 is less than the combined areas of overlap regions 470 and 472. Thus, TD OAR region 452 may receive higher dosage levels than initially expected at TP OAR region 402 if the TP treatment plan is carried out. Based on viewing TD image 450, TD OAR region 452, and TD treatment target area 454, a medical professional tasked with administering the treatment plan may decide to not provide the treatment, or may decide to alter the treatment plan before carrying it out.

Determining Organ Risk

Referring back to FIG. 1, and as described herein, treatment application computing device 108 may determine whether there is a risk to an organ of the patient based on one or more of the TP images, the target definition data, and one or more of the additional TD images.

For instance, in some examples, treatment application computing device 108 may determine a relative positioning of a target region to one or more OAR regions within a current image. As an example, treatment application computing device 108 may determine a distance between TD OAR region 452 and TD treatment target area 454. In some examples, the computed distance may be from an outermost edge of an OAR region to an outermost edge of a treatment target area (e.g., a closest distance). In some examples, the computed distance may be from a center of the OAR region to a center of the treatment target area. Treatment application computing device 108 may determine that an OAR dose constraint is violated if the computed distance is less than a predetermined threshold.

In other examples, treatment application computing device 108 may determine a relative positioning between an organ, such as an OAR, in an TP image and a later obtained TD image, and may determine that there is a risk to the organ if the organ has moved more than a predetermined distance. For instance, treatment application computing device 108 may determine a location (e.g., distance) of the organ in the TP image with respect to another organ, such as a location of one of structures 417, 419, 421 within TP image 400 with respect to another, and may further determine a location of the organ in the TD image, such as a location of the same structure 417, 419, 421 with respect to the same other structures 417, 419, 421 within TD image 450. Treatment application computing device 108 may then compare the locations of the TP image and the TD image to determine if the organ has moved more than a predetermined amount. For instance, treatment application computing device 108 may determine that an OAR dose constraint is violated if the organ has moved by more than a predetermined threshold (e.g., whether the organ has moved closer, or father, away from another organ by more than the predetermined threshold). For example, an OAR constraint may be violated if a heart has moved closer to an esophagus by at least 3 millimeters.

In some examples, treatment application computing device 108 determines a volume of an organ within the TP image, and a volume of the same organ within the TD image. Treatment application computing device 108 may determine that an OAR dose constraint is violated if the absolute value of a difference between the computed volumes is greater than a predetermined threshold.

Yet in other examples, the treatment application computing device 108 may determine a positioning (e.g., distance) between the target region and an organ, such as an OAR, in the TP image, and another relative positioning between the target region and the same organ in the TD image. The treatment application computing device 108 may determine that there is a risk to the organ based on the relative positioning determined for each of the TP and TD images.

For instance, the treatment application computing device 108 may compare (e.g., subtract) the determined relative positioning, and may determine an OAR dose constraint is violated based on the comparison (e.g., the difference is at or beyond a predetermined threshold)

In some examples, treatment application computing device 108 may compute one or more dose-volume histograms (DVHs) for one or more portions of an OAR region of a TP image, such as any of portions 455, 457, 459, 462 of TP OAR region 452 of TP image 450 (shown in FIG. 4B), and may determine whether one or more DVH dose constraints are violated based on the computed DVHs. For instance, treatment application computing device 108 may determine an expected dosage level within a TP overlap region of a TP image (e.g., an image taken during treatment planning), such as initial overlap region 420. Further, treatment application computing device 108 may determine an area of the initial overlap region 420 (shown in FIG. 4A), and may multiply the area by the dosage level expected within fourth portion 411 to determine the expected dosage level within TP overlap region 420. Similarly, treatment application computing device 108 determines a TD dosage level within the TD overlap regions 470, 472. For instance, treatment application computing device 108 may determine the dosage level within each of overlap regions 470, 472, and may add the dosage levels to determine the TD dosage level. Treatment application computing device 108 may compare the expected dosage level to the TD dosage level to determine whether a DVH dose constraint has been violated. For instance, treatment application computing device 108 may determine a difference between the TD dosage level and the expected dosage level, and may compare the difference to a predetermined threshold. If the difference is greater than the predetermined threshold, treatment application computing device 108 determines that a DVH dose constraint has been violated.

In some examples, treatment application computing device 108 may determine that a DVH dose constraint is violated when a portion of an OAR region is at risk to receive a dosage above a predetermined threshold (e.g., if the radiation dose prescribed by the treatment plan were administered to the target region). For instance, treatment application computing device 108 may determine that the OAR region overlaps with a portion of a current treatment target area, and may determine whether the dosage level associated with the portion of the current treatment target area is above a predetermined threshold. If the dosage level is above the predetermined threshold, treatment application computing device 108 determines that a DVH dose constraint is violated.

Generating Alerts

In some examples, treatment application computing device 108 displays an indication of whether any constraints are violated. For instance, as described herein, treatment application computing device 108 may determine whether any OAR or DVH dose constraints are violated, and may display, within a user interface, an indication of whether any of the OAR and DVH dose constraints have been violated.

Figure 5A:
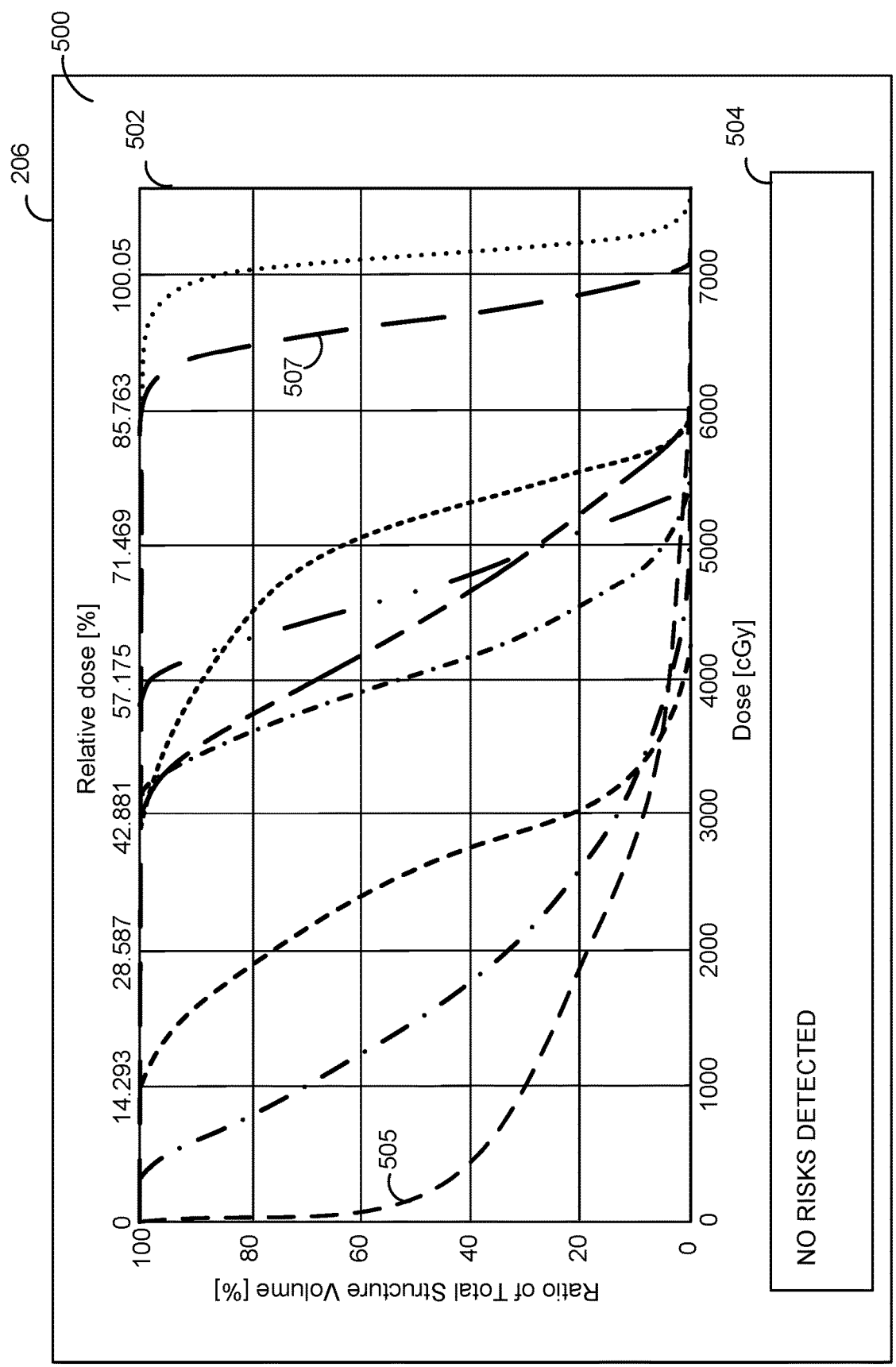
FIGS. 5A, 5B, and 5C illustrate portions of a graphical user interface identifying whether any risks with providing treatment have been identified, in accordance with some embodiments.

For example, FIG. 5A illustrates a graphical user interface (GUI) 500 that may be displayed by, for example, display 206. GUI 500 includes a DVH chart 502, and a risk alert pane 504. DVH chart 502 may include a plot of a computed DVH for each of one or more organs, or portions of organs. For instance, a first plot 505 may correspond to an esophagus, while a second plot 507 may correspond to the target volume. In this example, no constraints are violated. As such, risk alert pane 504 indicates that no risks were detected.

Figure 5B:
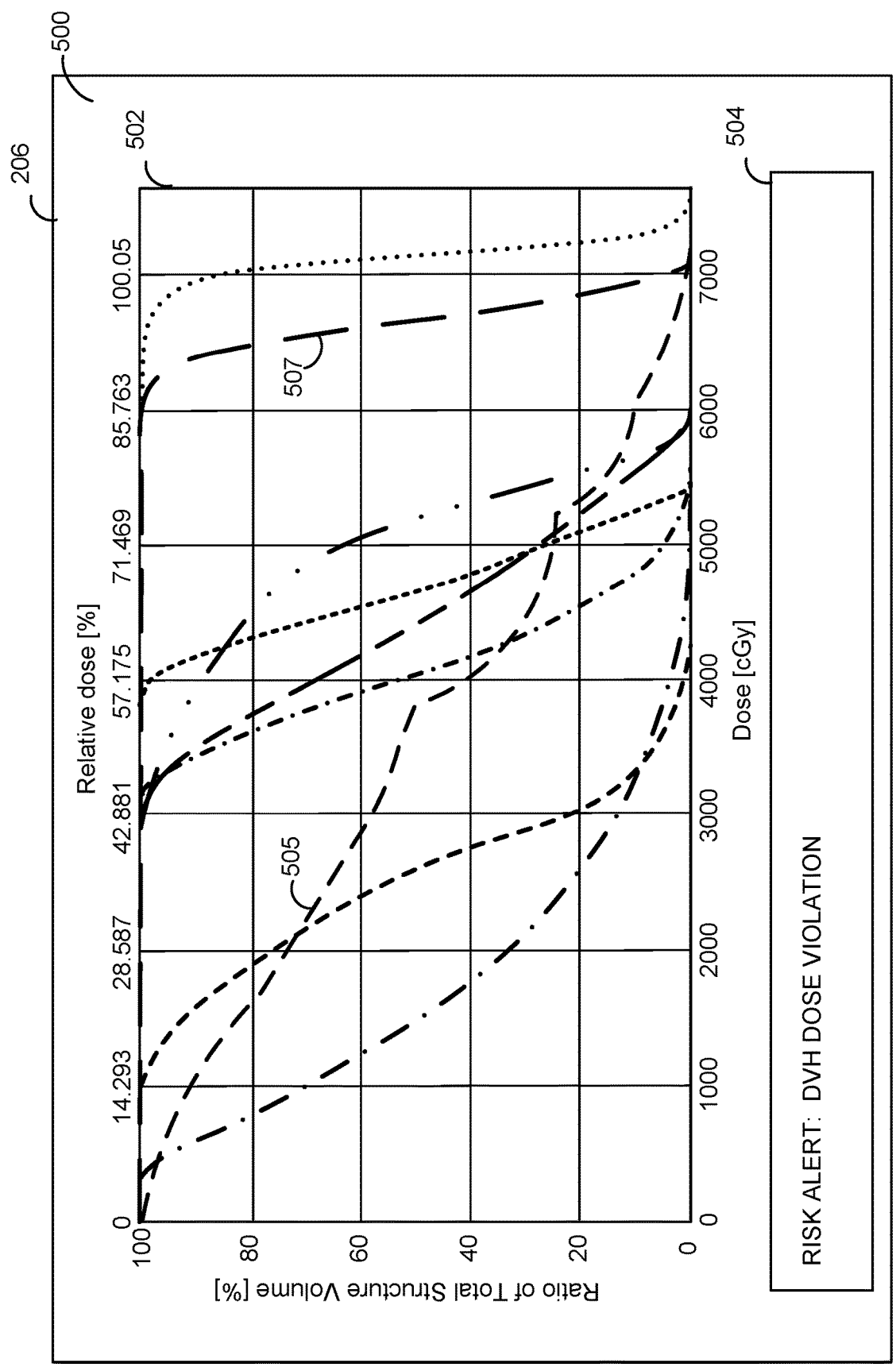
Figure 5C:
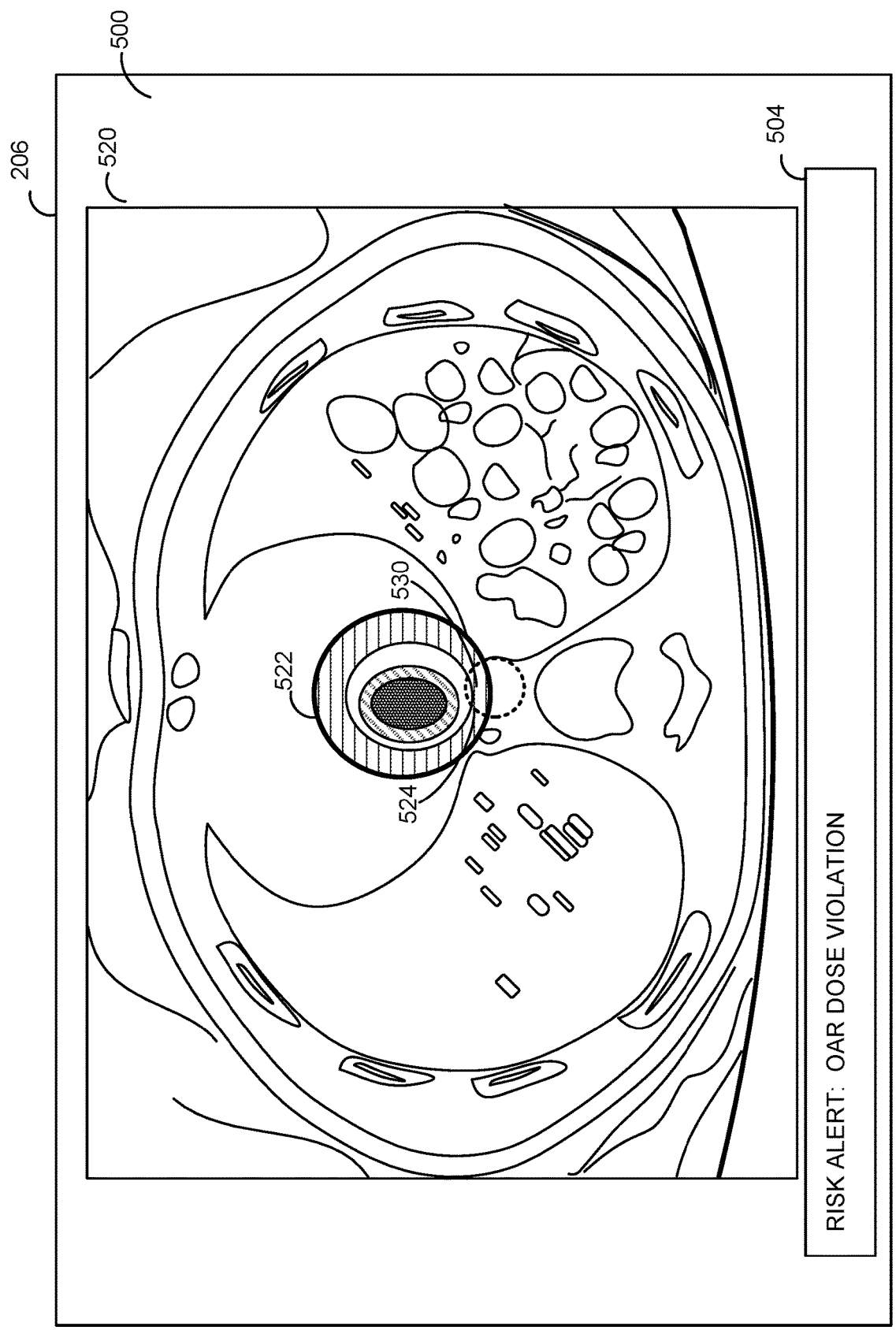

As illustrated in FIG. 5B, however, risk alert pane 504 of GUI 500 includes a risk alert that a dose threshold has been exceeded (a DVH dose constraint violation). In this example, the alert may have been generated based on the DVH computed for first plot 505, as it indicates that the esophagus may receive more dosage than that indicated in FIG. 5A. In FIG. 5C, GUI 500 displays a TD target area 522 and a TD OAR region 524, each superimposed over a TD image 520. In this example, treatment application computing device 108 may determine, for example, that an OAR dose constraint has been violated based on overlapping region 530 of TD target area 522 and TD OAR region 524. As such, treatment application computing device 108 may display a risk alert of an OAR dose violation within alert pane 504. In some examples, each risk alert is associated with an alert identification number (e.g., alert ID). For example, the exceeded dose threshold of FIG. 5B may be associated with an alert identification number of while the OAR dose violation of FIG. 5C may be associated with an alert identification number of 0x0100. The alert identification number identifies the specific constraint violated. Treatment application computing device 108 may display the corresponding alert identification number with each alert.

Referring back to FIG. 1, in some examples, a medical professional, such as a dosimetrist, may operate treatment planning computing device 106 to develop an initial treatment plan for a patient. For cardiac radioablation, the electrophysiologist may also be involved in developing the treatment plan. The initial treatment plan may be determined based on TP images obtained for the patient, and may identify an initial treatment target area, as well as expected dosage levels (e.g., DVHs) within the initial treatment target area. The patient may then be scheduled for treatment. On the day of treatment, before any dosage is applied, the patient is scanned to generate image data 103 characterizing a TD image having a field of view corresponding to the treatment area. Such scanning may be performed by a linac integrated kV-conebeam CT or any other type of scanner near or integrated with the treatment device 110. A current anatomical arrangement of the patient's organs, such as organs in the patient's thoracic region, are captured within the TD image. Treatment application computing device 108 may apply a transformation model to that image and the TD image to generate output data characterizing an anatomical change between the images. Based on the output data and the initial treatment target area, treatment application computing device 108 determines a current treatment target area within the current image. Further, treatment application computing device 108 determines expected dosage levels within the current treatment target area, and determines whether the current treatment target area includes any organs at risk (i.e., OARs).

In some examples, treatment application computing device 108 displays a comparison of the TP treatment target area with respect to the TP images, and the TD treatment target area with respect to the TD image, including any computed dosage levels. For example, treatment application computing device 108 may display expected dosage levels to any organs, including any organs being treated and any OARs. Further, and based on determined dosage levels to any OARs, treatment application computing device 108 may determine whether any constraints are violated (e.g., a specific dose threshold to an OAR is exceeded). Treatment application computing device 108 may provide an alert, such as an auditory or visual alert, if treatment application computing device 108 determines that a constraint is violated. In some examples, treatment application computing device 108 transmits a message, such as an email or SMS message, to one or more predetermined recipients identifying the alert.

Figure 3:
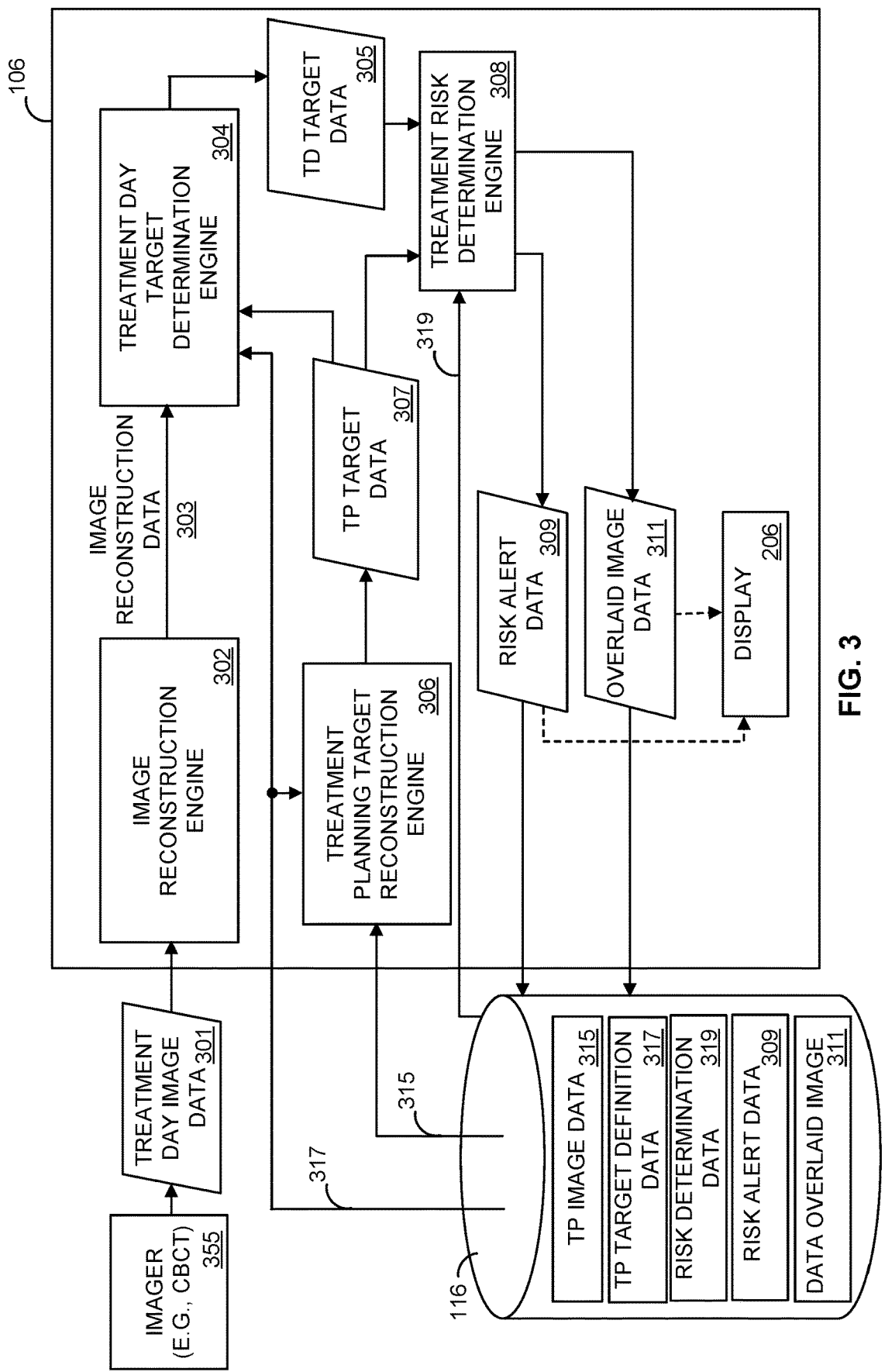
FIG. 3 illustrates exemplary portions of the treatment planning and application system of FIG. 1, in accordance with some embodiments.

FIG. 3 illustrates exemplary portions of treatment application computing device 108. In this example, treatment application computing device 108 includes image reconstruction engine 302, treatment day (TD) target determination engine 304, treatment planning (TP) target reconstruction engine 306, and treatment risk determination engine 308. In some examples, one or more of image reconstruction engine 302, treatment day (TD) target determination engine 304, treatment planning (TP) target reconstruction engine 306, and treatment risk determination engine 308 may be implemented in hardware. In some examples, one or more of image reconstruction engine 302, treatment day (TD) target determination engine 304, treatment planning (TP) target reconstruction engine 306, and treatment risk determination engine 308 may be implemented as an executable program maintained in a tangible, non-transitory memory, such as instruction memory 207 of FIG. 2, that may be executed by one or processors, such as processor 201 of FIG. 2.

In this example, database 116 stores TP image data 315, TP target definition data 317, and risk determination data 319, among other data. TP image data 315 characterizes TP images taken of a patient for treatment planning. TP target definition data 317 characterizes, for a corresponding initial image, a treatment area such as TP treatment target area 404, expected dosage levels within the treatment area, and may further characterize one or more OAR regions, such as TP OAR region 402. Further, risk determination data 319 may characterize risk data, such as constraints (e.g., OAR dose constraints and DVH dose constraints, rules) associated with risks to a treatment area.

TP planning target reconstruction engine 306 obtains TP image data 315 and TP target definition data 317 from database 116. Based on TP target definition data 317 and TP image data 315, TP planning target reconstruction engine 306 generates TP target data 307 characterizing a TP image that includes a TP treatment target area and one or more TP OAR regions. For instance, TP planning target reconstruction engine 306 may generate, based on TP target definition data 317, target area image data indicating the TP treatment target area, and may further generate, based on TP target definition data 317, TP OAR image data indicating an TP OAR region. TP planning target reconstruction engine 306 may overlay the target area image data and the TP OAR image data over the TP image characterized by TP image data 315 to construct a final TP output image, and may generate TP target data 307 characterizing the final TP output image.

Further, and on the day of treatment, a patient is scanned, for example, using imager 355 (e.g., a linear accelerator integrated kV-conebeam CT) to obtain treatment day image data 301. Image reconstruction engine 302 may obtain image data 301 for the patient, and, may reconstruct an image based on the obtained image data 301. In some examples, the reconstructed image may be a 3-dimensional image of one or more organs of the patient. Image reconstruction engine 302 generates image reconstruction data 303 characterizing the reconstructed image, and provides image reconstruction data 303 to target determination engine 304.

TD target determination engine 304 receives image reconstruction data 303 from image reconstruction engine 302, and further obtains TP target definition data 317 from database 116. TD target determination engine 304 also receives TP target data 307 from TP planning target reconstruction engine 306. Based on TP target data 307, TP target definition data 317, and image reconstruction data 303, TD target determination engine 304 generates TD target data 305 characterizing a TD image that includes a current treatment target area and one or more TD OAR regions. For instance, TD target determination engine 304 may determine a mapping between image reconstruction data 303 and TP target data 307 (e.g., based on identifying corresponding structures and applying a transformation model, as described herein). Further, and based on the TP treatment target area characterized by TP target data 307 and the determined mapping, TD target determination engine 304 generates TD target image data characterizing the TD treatment target area and, in some examples, TD OAR image data. In some examples, TP planning target reconstruction engine 306 receives input from a user (e.g., medical professional) identifying and characterizing the TD OAR region, as described herein, and generates the TD OAR image data based on the received input. TD target determination engine 304 may overlay the TD target image data and the TD OAR image data over the TD image characterized by image reconstruction data 303 to construct a final TD output image and may generate TD target data 305 characterizing the final TD output image.

Treatment risk determination engine 308 receives TD target data 305 from TD target determination engine 304 and TP target data 307 from TP planning target reconstruction engine 306, and further obtains risk determination data 319 from database 116. Treatment risk determination engine 308 also obtains risk determination data 319 from database 116, and generates risk alert data 309 characterizing one or more risk alerts based on the TD target data 305, TP target data 307, and risk determination data 319. For instance, risk determination data 319 may characterize one or more DVH dose constraints. Treatment risk determination engine 308 may determine on a relative positioning of an OAR within a TP image characterized by TP target data 307 and a current image characterized by TD target data 305, and may compute one or more dose-volume histograms (DVHs) based on the relative positioning. Further, treatment risk determination engine 308 may determine whether one or more of the DVH dose constraints are violated based on the DVHs. For example, treatment risk determination engine 308 may determine that a DVH dose constraint is violated if a portion of an OAR is at risk to receive a dosage above a predetermined threshold, characterized by the DVH dose constraint, if the radiation dose is applied to the target region.

In other examples, risk determination data 319 characterizes one or more OAR dose constraints. For instance, each OAR dose constraint may include a threshold value. In some examples, treatment risk determination engine 308 may determine a relative positioning between an organ, such as an OAR, in the TP image and the current image, and may determine that an OAR dose constraint is violated when the organ has moved more than a predetermined distance characterized by the OAR dose constraint. In some examples, treatment risk determination engine 308 may determine a positioning (e.g., distance) between the target region and an OAR in the TP image, and another positioning between the target region and the same OAR in the TD image. Treatment risk determination engine 308 may determine that an OAR dose constraint is violated based on the relative positioning determined for each of the TP and TD images. For instance, treatment risk determination engine 308 may compare (e.g., subtract) the determined relative positioning, and may determine that an OAR dose constraint is violated when the difference is at or beyond the predetermined threshold characterized by the OAR dose constraint.

In some examples, treatment risk determination engine 308 determines that an OAR dose constraint has been violated based on determining an overlapping region between a current target area and a current OAR region, such as overlapping region 530 of TD target area 522 and TD OAR region 524. For instance, treatment risk determination engine 308 may determine a dosage level corresponding to the overlapping region exceeds a predetermined threshold characterized by the OAR dose constraint. In some examples, treatment risk determination engine 308 determines an OAR dose constraint is violated when the overlapping region includes at least a predetermined percentage (e.g., 10%) of the current OAR region.

Treatment risk determination engine 308 may generate risk alert data 309 characterizing one or more risk alerts when a constraint (e.g., rule) is violated. For instance, risk alert data 309 may identify one or more of a constraint identification value (e.g., constraint ID), the TI image characterized by TP target data 307 (e.g., a corresponding TI image ID), and the TD image characterized by TD target data 305 (e.g., a corresponding TD image ID). Treatment risk determination engine 308 may store risk alert data 309 in database 116. In some examples, treatment risk determination engine 308 provides risk alert data 309 to display 206 for display.

Treatment risk determination engine 308 may further generate, based on TD target data 305 and TP target data 307, overlaid image data 311 characterizing an OAR region and a target area superimposed over an image, such as the TP image or the TD image. For instance, overlaid image data 311 may include a TD target area, such as TD target area 522, and a TD OAR region, such as TD OAR region 524, each superimposed over the TD image, such as TD image 520. In some examples, treatment risk determination engine 308 may generate overlaid image data 311 that includes the TD target area and the TD OAR region each superimposed over the TI image. In other examples, treatment risk determination engine 308 may generate overlaid image data 311 that includes the TD image superimposed over the TI image. Treatment risk determination engine 308 may store overlaid image data 311 in database 116. In some examples, treatment risk determination engine 308 provides overlaid image data 311 to display 206 for display.

Figure 6:
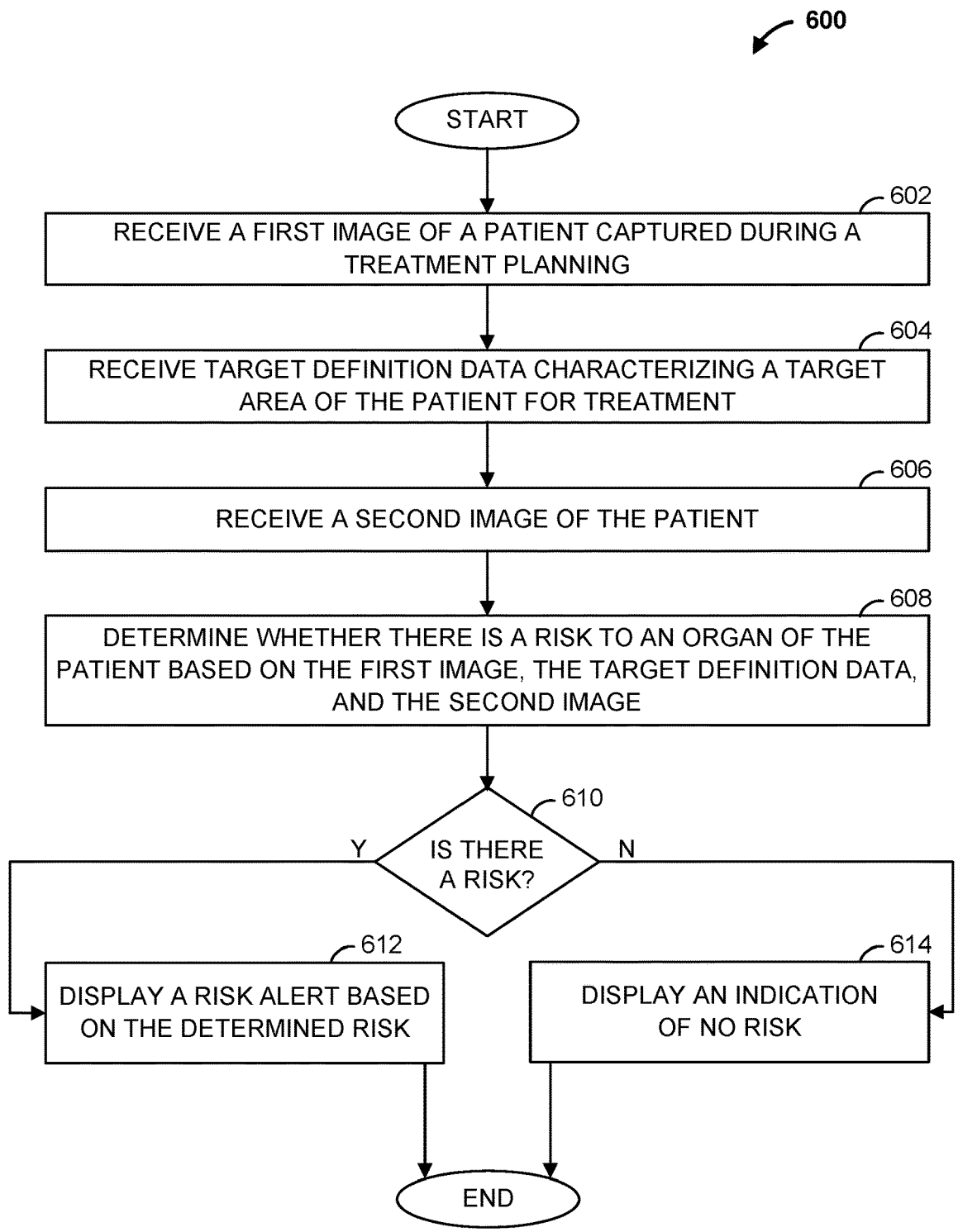
FIG. 6 is a flowchart of an example method to determine treatment risks, in accordance with some embodiments.

FIG. 6 illustrates a flowchart of an example method 600 that can be carried out by, for example, treatment application computing device 108. Beginning at step 602, treatment application computing device 108 receives a first image (e.g., a TP image) of a patient captured prior to treatment planning. The image may be, for instance, a CT image. The image may be stored in a database, such as database 116. On the day of treatment, treatment application computing device 108 may obtain the image (e.g., TP image data 315) from database 116. Further, and at step 604, treatment application computing device 108 may receive target definition data characterizing a target area of the patient for treatment. For instance, treatment application computing device 108 may obtain TP target definition data 317 corresponding to the obtained image.

Proceeding to step 606, treatment application computing device 108 may receive a second image (e.g., a TD image) of the patient. The image may be a conebeam CT image, for instance. At step 608, treatment application computing device 108 determines whether there is a risk to an organ of the patient based on the first image, the target definition data, and the second image. For instance, and as described herein, treatment application computing device 108 may determine whether a constraint, such as an OAR dose constraint or DVH dose constraint, is violated based on the first image, the target definition data, and the second image.

At step 610, if a risk is determined, the method proceeds to step 612, where a risk alert is displayed based on the determined risk. For instance, treatment application computing device 108 may determine generate risk alert data 309 based on one or more determined risks (e.g., constraint violations), and may provide at least portions of risk alert data 309 for display, such as to display 206. For instance, treatment application computing device 108 may provide for display within alert pane 504 an alert of "DVH DOSE VIOLATION" or "OAR DOSE VIOLATION." If, however, at step 610 no risks are determined, the method proceeds to step 614, where treatment application computing device 108 provides for display an indication of no risk. For instance, treatment application computing device 108 may provide for display within alert pane 504 an indication of "NO RISKS DETECTED." The method then ends.

Figure 7:
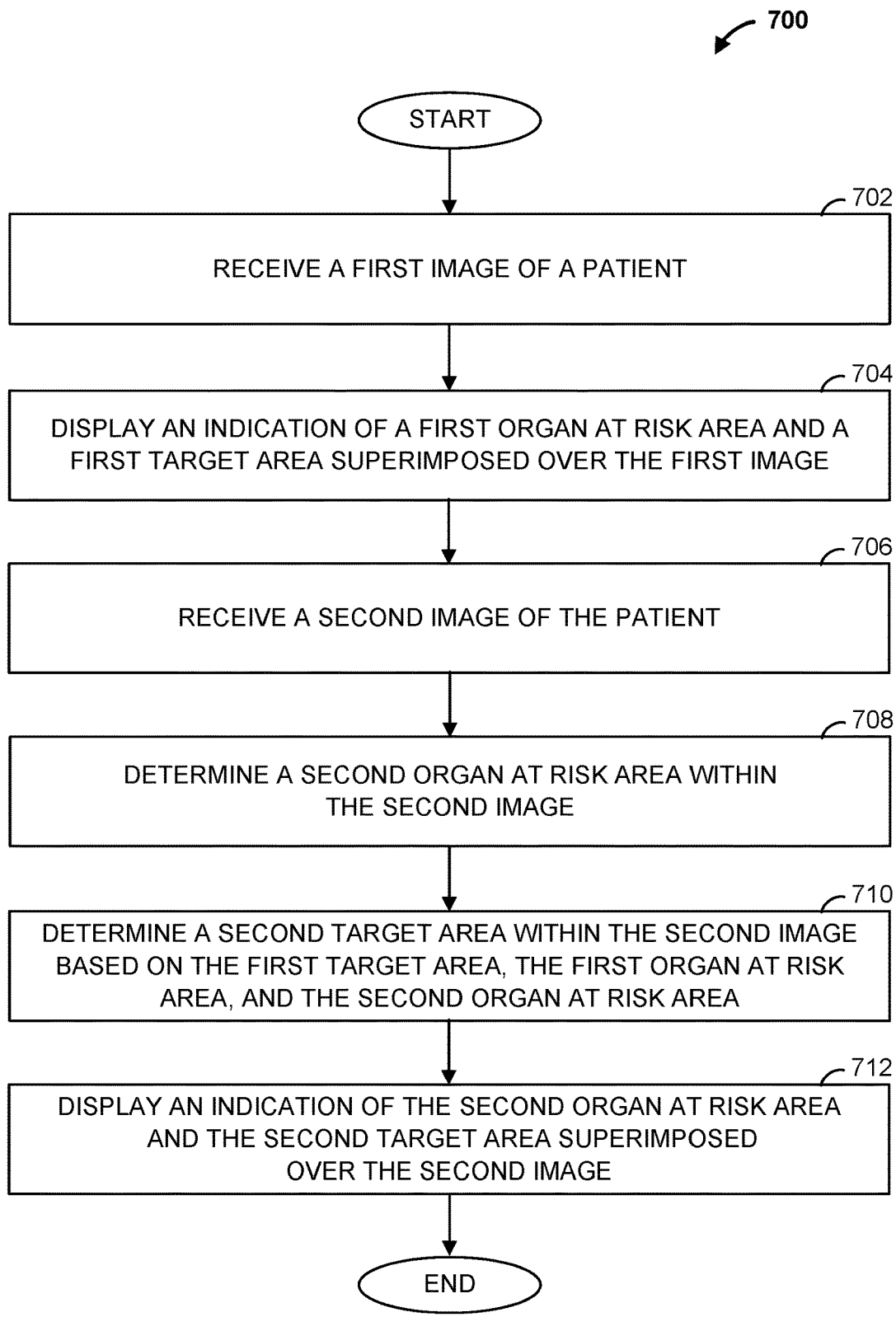
FIG. 7 is a flowchart of an example method to display computed target and OAR regions, in accordance with some embodiments.

FIG. 7 is a flowchart of an example method 700 that can be carried out by, for example, treatment application computing device 108. Beginning at step 702, treatment application computing device 108 receives a first image of a patient captured during treatment planning. For instance, prior to the day of treatment, a patient may lie on a table of image scanning device 102, and a TP image of the patient is captured. The TP image may be, for instance, a CT image. The TP image may be stored in a database, such as database 116. On the day of treatment, treatment application computing device 108 may obtain the image (e.g., TP image data 315) from database 116. At step 704, treatment application computing device 108 displays an indication of a first organ at risk area (e.g., TP OAR area) and a first target area (e.g., TP target area) superimposed over the first image. For instance, and as described herein, treatment application computing device 108 may display a TP OAR region 402, as well as an TP treatment target area 404, superimposed over the TP image 400.

Proceeding to step 706, treatment application computing device 108 receives a second image of the patient. For example, on the day of treatment, the patient may lie on the table of treatment 110, and be scanned to obtain a TD image. The patient may be scanned by the on-board imager of device 110 such that a conebeam CT image is obtained. At step 708, treatment application computing device 108 determines a second OAR area (e.g., TD OAR area) within the second image. For instance, treatment application computing device 108 may display the second image, and may further receive input from a medical professional that characterizes the second OAR area (e.g., the medical professional may "draw" the second OAR area on a user interface displaying the second image) or may be automatically contoured using known computational algorithms.

At step 710, treatment application computing device 108 determines a second target area (e.g., TD target area) within the second image based on the first target area, the first OAR area, and the second OAR area. For instance, and as described herein, treatment application computing device 108 may apply a transformation model to the first image and the second image to generate output data characterizing an anatomical change between the images. Based on the output data and the first target area, treatment application computing device 108 may determine the second target area within the second image.

Proceeding to step 712, treatment application computing device 108 displays an indication of the second OAR area and the second target area superimposed over the second image. For instance, treatment application computing device 108 may generate overlaid image data 311 that includes the second target area, such as TD target area 522, and the second OAR region, such as TD OAR region 524, each superimposed over the second image, such as TD image 520. Treatment application computing device 108 may provide the overlaid image data 311 to display 206 for display. The method then ends.

In some examples, a system comprises a database and a computing device communicatively coupled to the database. The computing device is configured to receive a first image (e.g., a TP image) of a patient. The computing device is also configured to receive target definition data characterizing a target area of the patient for treatment. Further, the computing device is configured to receive a second image (e.g., a TD image) of the patient. The computing device is also configured to determine whether there is a risk to an organ of the patient based on the first image, the target definition data, and the second image. The computing device is also configured to provide for display an indication of risk based on the determination.

In some examples, the first image is captured prior to the second image, and the second image is captured on a day of treatment. In some examples, the target definition data characterizes a first organ at risk area and a first treatment target area. In some examples, the computing device is configured to determine a second treatment target area based on the first organ at risk area, the first treatment target area, and a second organ at risk area. The second organ at risk area may include a same organ as the first organ at risk area.

In some examples, the computing device is configured to provide for display the first image, and receive input data characterizing the second organ at risk area. In some examples, the computing device is configured to determine a structure within the first image and the second image. The computing device is also configured to determine a mapping between the first image and the second image based on the structure. Further, the computing device is configured to determine the second treatment target area based on the mapping.

In some examples, the computing device is configured to determine an overlap region between the second treatment target area and the second organ at risk area. The computing device is also configured to determine the risk to the organ of the patient based on the overlap region. In some examples, the target definition data characterizes first dosage levels within the first treatment target area. In some examples the computing device is configured to determine a second dosage level within the overlap region, and determine the risk to the organ of the patient based on the second dosage level.

In some examples, the computing device is configured to superimpose the second treatment target area and the second organ at risk area over the second image. In some examples, the indication of risk comprises the second treatment target area and the second organ at risk area superimposed over the second image.

In some examples, a computer-implemented method comprises receiving a first image (e.g., a TP image) of a patient. The computer-implemented method also comprises receiving target definition data characterizing a target area of the patient for treatment. Further, the computer-implemented method comprises receiving a second image (e.g., a TD image) of the patient. The computer-implemented method also comprises determining whether there is a risk to an organ of the patient based on the first image, the target definition data, and the second image. The computer-implemented method further comprises providing for display an indication of risk based on the determination.

In some examples, the first image is captured prior to the second image, and the second image is captured on a day of treatment. In some examples, the target definition data characterizes a first organ at risk area and a first treatment target area. In some examples, the method further comprises determining a second treatment target area based on the first organ at risk area, the first treatment target area, and a second organ at risk area.

In some examples, the computer-implemented method comprises providing for display the first image, and receiving input data characterizing the second organ at risk area. In some examples, the computer-implemented method comprises determining a structure within the first image and the second image. The method also comprises determining a mapping between the first image and the second image based on the structure. Further, the method comprises determining the second treatment target area based on the mapping.

In some examples, the computer-implemented method comprises determining an overlap region between the second treatment target area and the second organ at risk area. The computer-implemented method also comprises determining the risk to the organ of the patient based on the overlap region.

In some examples, the target definition data characterizes first dosage levels within the first treatment target area. In some examples, the method comprises determining a second dosage level within the overlap region. In some examples, the method comprises determining the risk to the organ of the patient based on the second dosage level.

In some examples, the computer-implemented method comprises superimposing the second treatment target area and the second organ at risk area over the second image. In some examples, the indication of risk comprises the second treatment target area and the second organ at risk area superimposed over the second image.

In some examples, a non-transitory computer readable medium stores instructions that, when executed by at least one processor, cause the at least one processor to perform operations that comprise receiving a first image (e.g., a TP image) of a patient. The operations also comprise receiving target definition data characterizing a target area of the patient for treatment. Further, the operations comprise receiving a second image (e.g., a TD image) of the patient. The operations also comprise determining whether there is a risk to an organ of the patient based on the first image, the target definition data, and the second image. The operations further comprise providing for display an indication of risk based on the determination.

In some examples, the first image is captured prior to the second image, and the second image is captured on a day of treatment. In some examples, the target definition data characterizes a first organ at risk area and a first treatment target area. In some examples, the operations further comprise determining a second treatment target area based on the first organ at risk area, the first treatment target area, and a second organ at risk area.

In some examples, the operations comprise providing for display the first image, and receiving input data characterizing the second organ at risk area. In some examples, the operations comprise determining a structure within the first image and the second image. The operations also comprise determining a mapping between the first image and the second image based on the structure. Further, the operations comprise determining the second treatment target area based on the mapping.

In some examples, the operations comprise determining an overlap region between the second treatment target area and the second organ at risk area. The operations also comprise determining the risk to the organ of the patient based on the overlap region.

In some examples, the target definition data characterizes first dosage levels within the first treatment target area. In some examples, the operations comprise determining a second dosage level within the overlap region. In some examples, the operations comprise determining the risk to the organ of the patient based on the second dosage level.

In some examples, the operations comprise superimposing the second treatment target area and the second organ at risk area over the second image. In some examples, the indication of risk comprises the second treatment target area and the second organ at risk area superimposed over the second image.

In some examples, a system includes a means for receiving a first image of a patient. The system also includes a means for receiving target definition data characterizing a target area of the patient for treatment. Further, the system includes a means for receiving a second image of the patient. The system also includes a means for determining whether there is a risk to an organ of the patient based on the first image, the target definition data, and the second image. The system further includes a means for providing for display an indication of risk based on the determination.

In some examples, the first image is captured prior to the second image, and the second image is captured on a day of treatment. In some examples, the target definition data characterizes a first organ at risk area and a first treatment target area. In some examples, the system includes a means for determining a second treatment target area based on the first organ at risk area, the first treatment target area, and a second organ at risk area.

In some examples, the system includes a means for providing for display the first image, and receiving input data characterizing the second organ at risk area. In some examples, the system includes a means for determining a structure within the first image and the second image. The system also includes a means for determining a mapping between the first image and the second image based on the structure. Further, the system includes a means for determining the second treatment target area based on the mapping.

In some examples, the system includes a means for determining an overlap region between the second treatment target area and the second organ at risk area. The system also includes a means for determining the risk to the organ of the patient based on the overlap region.

In some examples, the target definition data characterizes first dosage levels within the first treatment target area. In some examples, the system includes a means for determining a second dosage level within the overlap region. In some examples, the system includes a means for determining the risk to the organ of the patient based on the second dosage level.

In some examples, the system includes a means for superimposing the second treatment target area and the second organ at risk area over the second image. In some examples, the indication of risk comprises the second treatment target area and the second organ at risk area superimposed over the second image.

Although the methods described above are with reference to the illustrated flowcharts, it will be appreciated that many other ways of performing the acts associated with the methods can be used. For example, the order of some operations may be changed, and some of the operations described may be optional.

In addition, the methods and system described herein can be at least partially embodied in the form of computer-implemented processes and apparatus for practicing those processes. The disclosed methods may also be at least partially embodied in the form of tangible, non-transitory machine-readable storage media encoded with computer program code. For example, the steps of the methods can be embodied in hardware, in executable instructions executed by a processor (e.g., software), or a combination of the two. The media may include, for example, RAMs, ROMs, CD-ROMs, DVD-ROMs, BD-ROMs, hard disk drives, flash memories, or any other non-transitory machine-readable storage medium. When the computer program code is loaded into and executed by a computer, the computer becomes an apparatus for practicing the method. The methods may also be at least partially embodied in the form of a computer into which computer program code is loaded or executed, such that, the computer becomes a special purpose computer for practicing the methods. When implemented on a general-purpose processor, the computer program code segments configure the processor to create specific logic circuits. The methods may alternatively be at least partially embodied in application specific integrated circuits for performing the methods.

The foregoing is provided for purposes of illustrating, explaining, and describing embodiments of these disclosures. Modifications and adaptations to these embodiments will be apparent to those skilled in the art and may be made without departing from the scope or spirit of these disclosures.

What is claimed is:

1. A system comprising:
   a database; and
   a computing device communicatively coupled to the database and configured to:
   receive a first image of a patient;
   receive target definition data characterizing a first treatment target area of the first image for treatment of the patient, and a first organ at risk area of the first image;
   receive a second image of the patient;
   determine a relative position between the first image and the second image based on at least one common structure within the first image and the second image;
   determine a second treatment target area of the patient based on the first treatment target area and the relative position;
   determine whether there is a risk to an organ of the patient based on the first organ at risk area, the second treatment target area, and a second organ at risk area of the second image; and
   provide for display an indication of the risk based on the determination.

2. The system of claim 1, wherein the first image is captured prior to the second image, and the second image is captured on a day of treatment.

3. The system of claim 1, wherein the computing device is configured to:
   provide for display the first image; and receive input data characterizing the second organ at risk area.

4. The system of claim 1, wherein the computing device is configured to:
  determine the at least one common structure within the first image and the second image;
  determine a mapping between the first image and the second image based on the at least one common structure; and
  determine the second treatment target area based on the mapping.

5. The system of claim 1, wherein the computing device is configured to:
  determine an overlap region between the second treatment target area and the second organ at risk area; and
  determine the risk to the organ of the patient based on the overlap region.

6. The system of claim 5, wherein the target definition data characterizes one or more dosage levels within the first treatment target area, and wherein the computing device is configured to:
  map a dosage level of the one or more dosage levels to the overlap region; and
  determine the risk to the organ of the patient based on the dosage level.

7. The system of claim 1, wherein the computing device is configured to:
  superimpose the second treatment target area and the second organ at risk area over the second image, wherein the indication of risk comprises the second treatment target area and the second organ at risk area superimposed over the second image.

8. The system of claim 1, wherein the computing device is configured to:
  determine a first distance between the first treatment target and the first organ at risk area;
  determine a second distance between the second treatment target and the second organ at risk area; and
  determine the risk to the organ of the patient based on the first distance and the second distance.

9. A computer-implemented method comprising:
  receiving a first image of a patient;
  receiving target definition data characterizing a first treatment target area of the first image for treatment of, and a first organ at risk area of the first image;
  receiving a second image of the patient;
  determining a relative position between the first image and the second image based on at least one common structure within the first image and the second image;
  determining a second treatment target area of the patient based on the first treatment target area and the relative position;
  determining whether there is a risk to an organ of the patient based on the first organ at risk area, the second treatment target area, and a second organ at risk area of the second image; and
  providing for display an indication of the risk based on the determination.

10. The computer-implemented method of claim 9 wherein the first image is captured prior to the second image, and the second image is captured on a day of treatment.

11. The computer-implemented method of claim 9 further comprising:
  providing for display the first image; and
  receiving input data characterizing the second organ at risk area.

12. The computer-implemented method of claim 9 further comprising:
  determining the at least one common structure within the first image and the second image;
  determining a mapping between the first image and the second image based on the at least one common structure; and
  determining the second treatment target area based on the mapping.

13. The computer-implemented method of claim 9 further comprising:
  determining an overlap region between the second treatment target area and the second organ at risk area; and
  determining the risk to the organ of the patient based on the overlap region.

14. The computer-implemented method of claim 13, wherein the target definition data characterizes one or more dosage levels within the first treatment target area, and wherein the method further comprises:
  mapping a dosage level of the one or more dosage levels to the overlap region; and
  determining the risk to the organ of the patient based on the dosage level.

15. The computer-implemented method of claim 9 further comprising:
  superimposing the second treatment target area and the second organ at risk area over the second image, wherein the indication of risk comprises the second treatment target area and the second organ at risk area superimposed over the second image.

16. The computer-implemented method of claim 9 further comprising:
  determining a first distance between the first treatment target and the first organ at risk area;
  determining a second distance between the second treatment target and the second organ at risk area; and
  determining the risk to the organ of the patient based on the first distance and the second distance.

17. A non-transitory computer readable medium storing instructions that, when executed by at least one processor, cause the at least one processor to perform operations comprising:
  receiving a first image of a patient;
  receiving target definition data characterizing a first treatment target area of the first image for treatment of the patient, and a first organ at risk area of the first image;
  receiving a second image of the patient;
  determining a relative position between the first image and the second image based on at least one common structure within the first image and the second image;
  determining a second treatment target area of the patient based on the first treatment target area and the relative position;
  determining whether there is a risk to an organ of the patient based on the first organ at risk area, the second treatment target area, and a second organ at risk area of the second image; and
  providing for display an indication of the risk based on the determination.

18. The non-transitory computer readable medium of claim 17 wherein the first image is captured prior to the second image, and the second image is captured on a day of treatment.

19. The non-transitory computer readable medium of claim 17 wherein the operations further comprise:
  providing for display the first image; and receiving input data characterizing the second organ at risk area.

20. The non-transitory computer readable medium of claim 17 wherein the operations further comprise:
determining a first distance between the first treatment target and the first organ at risk area;
determining a second distance between the second treatment target and the second organ at risk area; and
determining the risk to the organ of the patient based on the first distance and the second distance.

* * * * *